United States Patent [19]

Bennett et al.

[11] Patent Number: 4,902,630

[45] Date of Patent: Feb. 20, 1990

[54] FLUORESCENCE POLARIZATION IMMUNOASSY AND REAGENTS FOR MEASUREMENT OF C-REACTIVE PROTEIN

[75] Inventors: Larry G. Bennett, Grayslake; Enrico G. Chiapetta, Mundelein, both of Ill.

[73] Assignee: Abbott Laboratories, North Chicago, Ill.

[21] Appl. No.: 219,618

[22] Filed: Jul. 14, 1988

Related U.S. Application Data

[63] Continuation of Ser. No. 58,645, Jun. 3, 1987, abandoned, which is a continuation of Ser. No. 757,822, Jul. 22, 1985, abandoned.

[51] Int. Cl.$^4$ ............... G01N 33/566; G01N 33/536; G01N 33/542; G01N 33/533
[52] U.S. Cl. .................................. 436/546; 436/501; 436/536; 436/537; 436/800; 436/815
[58] Field of Search ............... 436/501, 536, 546, 800, 436/537, 815

[56] References Cited

U.S. PATENT DOCUMENTS

| | | |
|---|---|---|
| 4,447,545 | 5/1984 | DeFazio et al. |
| 4,492,762 | 1/1985 | Wang et al. |
| 4,504,585 | 3/1985 | Reynolds. |
| 4,681,859 | 7/1987 | Kramer. |

FOREIGN PATENT DOCUMENTS 2081257  2/1982  United Kingdom.

OTHER PUBLICATIONS

Chiapetta et al., *Clinical Chemistry*, 31(6):910, abstract no. 37 (Jun. 1985).
Dandliker et al., *Immunochemistry*, 1:165–191 (1964); 10:219–227 (1973).
Dandliker et al., *Biochemical and Biophysical Research Communication*, 5(4):299–304 (1961).
Grossman, *Journal of Clinical Chemistry*, 7(1):96–100 (Spring 1984).
Haber et al., *Biochemistry:Haber and Bennett*, 48:1935–1942 (1962).
Hind et al., *Internal Medicine for the Specialist*, 5(1):112–151 (Jan. 1984).
Jolley, *Journal of Analytical Toxicology*, 5:236–240 (1981).
Levison, et al., *Endo*, 99(4):1129–1143 (1976).
Maeda, *Clin. Chem.*, 24(12):2139–2144 (1978).
Spencer, et al., *Clin. Chem.*, 19(8):838–844 (1973).
Tengerdy, *The Journal of Immunology*, 99(1):126–132 (1967).
Killingsworth, *Clinical Chemistry*, 28(7):1621, abstract 364 (1982).

*Primary Examiner*—Robert J. Warden
*Assistant Examiner*—Jack Spiegel
*Attorney, Agent, or Firm*—Daniel W. Collins; Robert W. Stevenson

[57] ABSTRACT

This disclosure relates to a fluorescence polarization immunoassay method for determining C-reactive protein in liquids, especially in biological fluids such as serum, plasma, spinal fluid, amnionic fluid and urine. This disclosure also relates to novel reagents useful in such fluorescence polarization immunoassays.

4 Claims, No Drawings

4,902,630

FLUORESCENCE POLARIZATION IMMUNOASSY AND REAGENTS FOR MEASUREMENT OF C-REACTIVE PROTEIN

This is a continuation of application Ser. No. 058,645, filed June 3, 1987, abandoned, which is a continuation of application Ser. No. 757,822, filed July 22, 1985, now abandoned.

BACKGROUND OF THE INVENTION

1. Technical Field

The present invention relates generally to a method, and reagents useful in the method, for determining ligands in liquids, especially biological fluids such as serum, plasma, spinal fluid, amnionic fluid and urine. The present invention relates more particularly to a novel fluorescence polarization immunoassay for C-Reactive Protein, and novel reagents useful in the assay.

2. Background Art

Competitive binding immunoassays for measuring ligands are well known, and are based on the competition between a ligand in a test sample and a labeled reagent, referred to as a tracer, for a limited number of receptor binding sites on antibodies specific to the ligand and tracer. The concentration of ligand in the sample determines the amount of tracer that will specifically bind to an antibody. The amount of tracer-antibody complex produced can be quantitatively measured and is inversely proportional to the quantity of ligand in the test sample.

Fluorescence polarization immunoassay techniques are based on the principle that a fluorescent labeled compound, when excited by plane polarized light, will emit fluorescence having a degree of polarization inversely related to its rate of rotation. Specifically, when a molecule such as a tracer-antibody complex having a fluorescent label is excited with plane polarized light, the emitted light remains highly polarized because the fluorophore is constrained from rotating between the time when light is absorbed and when it is emitted. When a "free" tracer compound (i.e., unbound to an antibody) is excited by plane polarized light, its rotation is much faster than that of the corresponding tracer-antibody complex; therefore, the emitted light is depolarized to a much greater extent. Thus, fluorescence polarization provides a quantitative means for measuring the amount of tracer-antibody complex produced in a competitive binding immunoassay.

Fluorescence polarization techniques have been applied to U.S. Patent No. 4,420,568 to Wang, et al., commonly assigned herewith, which is directed to the use of a triazinylamino-fluorescein moieties as fluorophores. Various other fluorescent labeled compounds are known in the art. For example, U.S. Patent No. 3,998,943 describes the preparation of a fluorescently labeled insulin derivative using fluorescein isothiocyanate (FITC) as the fluorescent label and a fluorescently-labeled morphine derivative using 4-aminofluorescein hydrochloride as the fluorescent label. Carboxyfluorescein has also been used for analytical determinations. R. C. Chen, Analytical Letters, 10, 787 (1977) describes the use of carboxyfluorescein to indicate the activity of phospholipase. The carboxyfluorescein is described as encapsulated in lecithin liposomes, and as fluorescing only when released by the hydrolysis of lecithin. U.S. Patent No. 4,476,229 to Fino, et al., also commonly assigned herewith, describes a series of amino acid amido derivatives of carboxyfluorescein useful as reagents in fluorescence polarization immunoassays.

As previously explained, fluorescence polarization techniques are based on the principle that a fluorescent labeled compound in solution, when excited by plane polarized light, will emit fluorescence having a degree of polarization related to its molecular rotational relaxation time. The molecular rotational relaxation time, and hence the magnitude of the fluorescence polarization response, is directly related to the molecular size of the compound. Accordingly, when plane polarized light is passed through a solution containing a relatively high molecular weight fluorescent compound, the degree of polarization of the emitted light will in general be greater than when plane polarized light is passed through a solution containing a low molecular weight fluorescent compound.

The fluorescence polarization principle is ordinarily utilized in an assay by mixing a sample containing an analyte (or suspected of containing an analyte) with a "tracer,", i.e., a labelled compound similar to the analyte but capable of producing a fluorescence polarization response to plane polarized light. Conventionally, the analyte is a relatively low molecular weight compound, i.e. less than about 2,000 daltons. Antibody specific to the analyte and the tracer is also included in the mixture. The tracer and the analyte compete for a limited number of receptor binding sites on the antibody. The amount of tracer that will bind is inversely related to the concentration of analyte in the sample, because the analyte and tracer each bind to the antibody in proportion to their respective concentrations.

The principle of fluorescence polarization has been successfully applied because it is known that the fluorescence polarization response of an assay solution to plane polarized light will give a quantitative indication of the relative amount of free and bound tracer, because of the discrepancy in molecular size between the former and the latter. The free tracer (i.e., the tracer in solution when not complexed to the antibody) is generally a relatively small molecule compared to the tracer-antibody complex, and thus will tend to exhibit a shorter rotational relaxation time, such that the incident plane polarized light becomes depolarized. In contrast, plane polarized light interacting with bound tracer will tend to remain highly polarized because the large antibody-tracer rotates very little between the time that light is absorbed and emitted.

However, fluorescence polarization techniques have been only applied with reasonable success to the measurement of analytes of relatively low molecular weight. Since the tracer employed must generally resemble the analyte in order to compete effectively for antibody receptor sites, the tracer itself, in such instances, will be relatively large and will tend to retain the polarization of plane polarized light. This approach of doing a competitive binding immunoassay using a fluorescein-labeled compound as the tracer generally works well because of the substantial difference in polarization observed when the tracer is free versus when it is bound by specific antibody. A polarization unit change from 0.02 (free) 0.20 (bound) can be considered typical of many sun tracers.

When a large tracer molecule is bound to an antibody, there will generally not be an appreciable difference in the fluorescence polarization response when compared with the response produced by the free tracer, so that in cases where it has heretofore been desired to measure relatively large molecular weight analytes, i.e., on the order of greater than about 100,000 daltons, it has been generally necessary to consider alterative assay techniques, such as nephelometry. A few examples of fluorescence polarization immunoassays applied to quantitation of higher molecular weight (treater than about 10,000 daltons) substances can be found. Some literature demonstration such assays are H. Maeda, Clin. Chem. 24:2139 (1978); W. B. Dandliker, et al., Immunochemistry 10:219 (1973); and S. A. Levison, et. al., Endocrinology 99:1129 (1976). However, notable features of these disclosures of polarization assays of relatively low molecular weight proteins (less than 100,000 daltons) are the small polarization changes observed when the tracer if free versus when it is bound by antibody. Typically the polarization changes observed a only in the range of 0.015 to 0.045 polarization units.

In contrast, the CRP/fluorescein conjugate tracer described in this disclosure (M.W. 120,000 daltons) exhibits a polarization change of slightly more than 0.10 polarization units.

Nephelometric techniques have been found to provide a satisfactory means for measuring the light scattered from a solution containing large molecules or suspended particles. In accordance with these techniques, incident light is passed through a solution, a portion of the incident light is scattered, and then the amount of scattered light is measured. These techniques have application, for example, when immunoprecipitation assays are conducted. In such assays, antibodies are raised to the analyte, often forming large three-dimensional lattices. These lattices produce an increase in the light scattering properties of the solutions.

The TDX@ Fluorescence Polarization Analyzer, an instrument commercially available from Abbott Laboratories, Abbott Park, Illinois, for example, provides the capability of automation of fluorescence polarization assays, and, with minor modification of the instrument, of nephelometric analysis, as well as other systems of analysis. However, it would be desirable and useful to be able to perform fluorescence polarization techniques to measure large molecules, so that, among other reasons, the modifications which are necessarily made to such analyzers to enable them to perform nephelometric as well as fluorescence polarization assays would be unnecessary; assays of large molecular weight species could then be performed using such readily available, unmodified analytical instrumentation.

C-reactive protein (CRP) is a large molecular weight species which it would be advantageous to measure by fluorescence polarization techniques, so that nephelometric or other more complex assay systems would be unnecessary. CRP is a plasma protein synthesized by hepatocytes and is present in the serum of healthy subjects in trace amounts. It is acute-phase protein; within hours of an acute injury or the onset of most types of infection or inflammation, its rate of synthesis and secretion in subjects increases markedly, with a resultant rise in the serum concentration. The amount of the rise has been found to correlate well with the severity of tissue damage.

Precise measurement of serum CRP concentration provides the clinician with a sensitive indication of many diseases. This is of value both in the initial evaluation of a disorder and in monitoring its response to therapy. However, CRP assays fall into a different category from the vast majority of in vitro diagnostic tests, since CRP concentration provides a screening test for organic disease and an indication of disease activity when the diagnosis is known, rather than a indication of a given disease state.

The CRP molecular (molecular weight 120,000) consists of five identical nonglycosylated polypeptide subunits. The capacity of CRP to bind a wide range of different ligands is presumably central to its in vivo function. Thus CRP is conventionally detected and quantitated by various immunological methods. Tests based on the interaction between CRP and pneumococcal C polysaccharide, and capillary tube precipitation methods involving anti-CRP serum, are well known. The simpliest current method is a latex-agglutination procedure, in which latex particles coated with anti-CRP antibodies are agglutinated by CRP in the serum. Although quite sensitive (detection limit about 5 mg/l) and rapid, the latex test is only qualitative, and is subject to technical problems and interferences. Accordingly, it does not provide as valuable information as that furnished by precise, quantitative methods.

The classic immunochemical techniques of radial immunodiffusion and electroimmunoassay can be used to measure CRP accurately and with suitable sensitivity, but they are slow and technically demanding for routine work. Ideally, a CRP assay should be rapid and technically simple, yield a accurate result, and be capable of automation for large-scale use. A number of such systems are commercially available based on either homogeneous enzyme, fluoroimmunoassay or rate immunephelometry. However, heretofore the economy, ease of performance and simplicity of quantitation of CRP by fluorescence polarization immunoassay has not been known, because of the aforedescribed constraints placed upon such techniques by the relatively large size of the CRP molecule.

SUMMARY OF THE INVENTION

The present invention offers an advance in the art of detection of the presence of amount of CRP in a biological sample. The instant invention encompassesa fuorescence polarization assay and reagents useful in the assay for CRP. In particular the invention described herein provides the advantages of the fluorescence polarization techniques previously set forth, for the movelmeasurement of CRP levels and encompases a method for determining CRPs in a sample comprising:

(a) intermixing with the sample a fluorescent tracer having a ligand analog to CRP; and wherein the ligand analog has a maximum of one common epitope with the ligand so as to be specifically recognizable by a common antibody or other receptor binding site; and an antibody capable of specifically recognizing said ligand and said tracer, whereby a tracer-antibody complex is formed; and (b) determining the amount of tracer-antibody complex formed in step (a) by fluorescence polarization technique, as a measure of the concentration of the ligand in the sample.

The invention further encompasses certain novel reagents useful in the above-described method.

DETAILED DESCRIPTION OF THE INVENTION

Definitions

The term "ligand", as used herein, refers to a molecule, to which a binding protein, such as a receptor or an antibody, can be obtained or formed. The ligand of interest in the present invention is CRP. Such haptens are protein-free compounds, generally of low molecular weight, which do not induce antibody formation when injected into an animal, but which are reactive to antibodies. Antibodies to haptens are generally raised by first conjugating the haptens to a protein and injecting the conjugate product into an animal. The resulting antibodies are isolated by conventional, well-known antibody isolation techniques.

The term "ligand-analog", as used herein, refers to a mono- or polyvalent radical, a substantial portion of which has the same spatial and polar organization as the ligand to define one or more determinant or epitopic sites capable of competing with the ligand for the binding sites of a receptor. A characteristic of such ligand-analog is that it possesses sufficient structural similarity to the ligand of interest so as to be recognized by the antibody for the ligand. For the most part, the ligand-analog will have the same or substantially the same structure and charge distribution (spatial and polar organization) as the ligand of interest (for purposes of the present invention, CRP) for a significant portion of the molecular surface. Since frequently, the linking site for a hapten will be the same in preparing the antigen for production of antibodies as that used in the tracer for linking to the ligand, the same portion of the ligand analog which provides the template for the antibody will be exposed by the ligand analog in the tracer.

The present invention involves the use of fluorescein and derivatives of fluorescein. In particular, a necessary property of fluorescein and its derivatives for the usefulness of the tracer compounds is the fluorescence of fluorescein. These compounds provide the fluorescent response when excited by polarized light of an appropriate wavelength, thereby to enable the fluorescence polarization measurement to be made. Generally, the tracer compounds used in the assay provided by the present invention exist in solution as biologically acceptable salts such as sodium, potassium, ammonium and the like, which allows the compounds to exist in the open, fluorescent form, when employed in the analytical methods of the present invention. The specific salt present depends on the buffer employed to adjust the pH level. for example, in the presence of a sodium phosphate buffer, the compounds utilized in the present invention will generally exist in the open form, as a sodium salt. Suitable fluorescein tracer compounds for use in the invention include, for example, carboxyfluorescence fluorescein isothiocynates (FITC), triazinylaminofluoresceins (DTAF) and many other compounds well known in the art, including those disclosed in the art previously cited. The selection of a particular fluorescent tracer for use is a matter of choice for the routine, given the teachings hereof, and is not crucial to the practice of the present invention.

Fluorescence Polarization Immunoassay

In accordance with the method of the present invention, a sample containing CRP is intermixed with a tracer and an antibody specific for the CRP and the tracer. The CRP present in the sample and the tracer compete for a limited number of antibody sites, resulting in the formation of CRP-antibody and tracer-antibody complexes. By maintaining constant the concentration of tracer and antibody, the ratio of CRP-antibody complex to tracer-antibody complex that is formed is directly proportional to the amount of CRP present in the sample. Therefore, upon exciting the mixture with polarized light and measuring the polarization of the fluorescence emitted by a tracer and a tracer-antibody complex, one is able quantitatively to determine the amount of CRP in the sample.

A tracer in solution which is not complexed to an antibody is free to rotate in less than the time required for absorption, and re-emitted light is relatively randomly oriented so that the fluorescence polarization of a tracer not complexed to an antibody is low, approaching zero. Upon complexing with a specific antibody, the tracer-antibody complex thus formed assumes the rotation of the antibody molecule which is slower than that of the relatively small tracer molecule, thereby increasing the polarization observed. Therefore, when a ligand competes with the tracer for antibody sites, the observed polarization of fluorescence of the resulting mixture of the free tracer and tracer-antibody complex assumes a value intermediate between that of the tracer and that of the tracer-antibody complex. If a sample contains a high concentration of the ligand, the observed polarization value is closer to that of the free ligand, i.e., low. If the test sample contains a low concentration of the ligand, the polarization value is closer to that of the bound ligand, i.e., high. By sequentially exciting the reaction mixture of an immunoassay with vertically and then horizontally polarized light and analyzing only the vertically polarized component of the emitted light, the polarization of fluorescence in the reaction mixture can be accurately determined. The precise relationship between polarization and concentration of the ligand to be determined is established by measuring the polarization values of calibrators with known concentrations. The concentration of the ligand can be interpolated from a standard curve prepared in this manner.

The pH at which the method of the present invention is practiced must be sufficient to allow the tracers to exist in their ionized state. The pH may range from about 3 to 12, more usually in the range of from about 5 to 10, most preferably from about 6 to 9. Various buffers can be used to achieve and maintain the pH during the assay procedure. Representative buffers include borate, acetate, phosphate, carbonate, tris, barbital and the like. The particular buffer employed is not critical to the present invention, but in an individual assay, a specific buffer may be preferred in view of the antibody employed and ligand to be determined. The cation portion of the buffer will generally determine the cation portion of the tracer salt in solution.

The methods of the present invention are practiced at moderate temperatures and preferably at a constant temperature. The temperature will normally range from about zero degrees to about 50 degrees C, more usually from about 15 degrees to about 40 degrees C.

The concentration of CRP which can be assayed in accordance with the invention will generally vary from about $10^{-2}$ to about $10^{-13}$ M, more usually from about $10^{-4}$ to about $10^{-10}$ M. High concentrations of CRP can be assayed upon dilution of the original sample.

In addition to the concentration range of CRP, considerations such as whether the assay is qualitative, semiquantitative or quantitative, the equipment employed, and the characteristics of the tracer and antibody will normally determine the concentration of the tracer and antibody which is used. While the concentration range of CRP in the sample will determine the range of concentration of the other reagents, i.e., tracer and antibody, normally to optimize the sensitivity of the assay, individual reagent concentrations will be determined empirically. Appropriate concentrations of the tracer and antibody are readily ascertained by one of ordinary skill in the art.

Although not forming part of the present invention, it is to be appreciated that the fluorescence polarization immunoassay for CRP provided by the present invention can be performed especially advantageously using reagents and assay procedures, in accordance with the invention, on a TDx (registered trademark) Fluorescence Polarization Analyzer, commercially available from Abbott Laboratories, Abbott Park, Illinois, from whom full details concerning operation and features of this Analyzer are available.

As previously mentioned, the fluorescence polarization immunoassay approach has not heretofore been commercially applied to quantitation of high molecular weight substances such as proteins because of the generaly accepted notion that the observed difference in polarization between the free tracer (fluorescein-labeled protein) and the bound tracer (fluorescein-labeled protein—antibody complex) would be unacceptably low. In the development of the instant invention, such was found not to be the case when fluorescein-labeled CRP was incubated with goat, rabbit, or sheep anti-CRP antiserum. A polarization change in excess of 0.100 units (reproducibility 0.003) has been observed when fluorescein-labeled CRP is incubated with excess anti-CRP antisera. This observed polarization change unexpectedly was found to be of sufficient magnitude to enable the development of a homogeneous fluorescence polarization immunoassay for quantitation of elevated levels of CRP in human serum or plasma.

There are several considerations involved in making a CRP/fluorescein conjugate that will work sufficientlywell as a tracer in a fluorescence polarization immunoassay. Among the important factors which must be considered are:

(1) functional groups of the CRP protein (i.e. constituent amino acid residues) which may be derivatized without denaturing the protein or masking its major antigenic determinants.

(2) the degree of fluorescein substitution on CRP.

(3) length and flexibility of the spacer arm between the protein "surface" and attached fluoresceins' absorption/emission dipoles.

Experimentation in connection with the present invention has shown that fluorescein derivatives that couple primarily with amine groups of the CRP result in preferred tracers in terms o f assay performance while causing the least amount of protein denaturation and/or crosslinking and precipitation, and that there is an optimum number of fluorescein molecules which, when coupled to a CRP molecule, provide the best tracer in terms of achieving maximum assay span. This optimum level of substitution is around 1–2 moles of fluorescein per mole of CRP. In addition, further experimentation has shown that the bifunctional triazine ring which couples fluoresceinamine to CRP, e.g., as in DTAF/CRP conjugates previously mentioned, provides optimum spacer arm length and rigidity and is therefore most preferred for use in producing a fluorescein-labeled CRP tracer.

Accordingly, it has been found that when 5(4,6-dichlorotriazin-2-yl)-amino fluorescein (DTAF) is reacted with human CRP under appropriate conditions, suitable fluorescein/CRP conjugates are obtainable for use as tracers in a fluorescence polarization immunoassay in accordance withthe invention. A general, preferred procedure for accomplishing this follows.

(1) Human CRP was dissolved in 0.1M borate buffer, pH 8.5, at a concentration of 2 mg/ml.

(2) DTAF was dissolved in demethylformamide at a concentration of 1 mg/ml.

(3) Sufficient DTAF solution was added to the CRP solution such that a 20 to 1 molar excess of DTAF to CRP was achieved. The reaction mixture was vortexed and allowed to stand at room temperature for two hours. The reaction mixture was then chromatographed over a short column of Sephadex G-25 to remove unreacted DTAF. The fluorescent material eluting in the voidvolume was the DTAF/CRP conjugate. Dialysis of the conjugate against phosphate buffered saline provided a tracer of sufficient purity that it could be diluted with buffer and used directly in a fluorescence polarization immunoassay for quantitation of unlabeled human CRP in serum or plasma samples.

EXAMPLES

The following examples describe experiments which were performed in accordance with the concepts of the present invention, and are directed to assays for CRP using fluorescence polarization techniques. Such assays can be conducted in accordance with the following general procedure:

(1) A measured volume of standard or test serum is delivered into a test tube and diluted with buffer;

(2) A known concentration of a tracer optionally containing a surfactant is then added to each tube;

(3) A known concentration of antisera is added to the tubes;

(4) The reaction mixture is incubated at room temperature; and (5) The amount of tracer bound to antibody is measured by fluorescence polarization techniques as a measure of the amount of ligand in the sample.

A fluorescence polarization immunoassay for CRP can be performed on a TDx Analyzer without prior sample pretreatment, as is usually required for prior art nephelometric assays, and in a much shorter time period than radial immunodiffusion, radioimmunoassay or enzyme immunoassay techniques. Moreover, the reagents of the invention have been found to be stable and relatively easy to manufacture. Although the principles of the invention fully are applicable to non-automated assays, the automated nature of TDx assays assures minimal technician time to perform assays or interpret data.

EXAMPLE 1

A prototype, general homogeneous fluorescence polarization immunoassay for human CRP was performed as follows according to the present invention:

Reagents:
(1) Goat anti-human CRP antiserum
(2) DTAF labeled CRP diluted in a suitable buffer (as previously described)
(3) Calibrators with known concentrations of CRP in serum.

Protocol for prototype assay:

An appropriate dilution of goat anti-human CRP antiserum in 1.8 ml was added to each of six 12 mm×75 mm disposable test tubes. The equivalent of 2 microliters of each CRP calibrator was added to each respective tube and then vortexed. The incubation of the sample with antiserum was allowed to proceed for 10 minutes during which time a background fluorescence reading was made on each sample and stored in the computer memory of the TDx Analyzer.

Ten minutes after each calibrator sample had been added to each antiserum dilution, 25 ul of the DTAF/CRP conjugate tracer, of appropriate concentration, was added to each respective sample. The samples were mixed well and allowed to stand an additional 8 minutes before reading each sample sequentially in the Analyzer. The TDx Analyzer is capable of automatically subtracting out background fluorescence and printing out corrected polarization values for each sample.

EXAMPLE 2

Automated C-Reactive Protein Assay by Fluorescence Polarization Immunoassay

Isolation of Human C-Reactive Protein

CRP was obtained from malignant ascitic and pleural fluids by calcium-dependent affinity chromatography on pneumococcal C-polysaccharide covalently coupled to cyanogen bromide-activated Sepharose. It was then gel filtered on Ultrogel AcA44 (acrylamide-agarose beads) in the presence of calcium ions, combining molecular sieve chromatography with removal of contaminating SAP by its affinity for agarose. Residual trace contaminants were removed by immunoabsorption with anti-normal human serum and anti-SAP antibodies insolubilised on Sepharose and by absorption with Sepharose-Con A to remove glycoproteins and Blue-Sepharose to remove albumin. After a final gel filtration step on Sephaclyl S-300, between 35-40% of the initial CRP was recovered in substantially pure form.

CRP Antisera Production

Sheep and goats were immunized by deep subcutaneous or intramuscular injections of isolated CRP emulsified in complete Freund's adjuvant, followed by biweekly or monthly booster injections of emulsions in incomplete adjuvant. Each injection contained at least 500 micrograms CRP. This regiment was followed for all animals for a five month period while the animals were monitored for antibody titer at biweekly or monthly bleeding intervals. Booster injections were then interrupted for three months while titer monitoring continued. Following the three months rest, boosting was resumed as titers were beginning to drop.

Tracer Synthesis DTAF/CRP

A stock solution of 5-(4,6-dichloro-triasin-2-yl)-Amino Fluorescein, (DTAF) was prepared in absolute ethanol with the aid of sonification, at 2 mg/ml. Stock CRP contained in 0.005 Molar Borate buffer, pH 9.0, 0.002 Molar $CaCL_2$ and 0.9% NaCl at 3 m g/ml, is made to a concentration of 500 micrograms in 0.04 Molar Borate buffer pH 9.0, .002 M $CaCl_2$, .9% NaCl. To 1 ml of the (500 micrograms/ml) CRP solution, 25 microliters of stock DTAF are added. The coupling reaction was then carried out for 1 hour at ambient temperature with mixing, in the dark. At the end of the 1 hour period, the DTAF reaction was quenched with 50 μl of 10% glycine prepared in .04 Molar Borate buffer pH 9.0 (same buffer as above), and incubated with mixing for 15 minutes at the above conditions. The conjugate was chromatographed over sephodex G-25 and eluted with Borate buffer pH 9,0 (same buffer as above) and collected at void volume. It was then diluted to a desired concentration for use in an automated assay on the TDx Analyzer.

Automated C-Reactive Protein Assay Reagents, Calibrators and Controls

Tracer:

The stock DTAF/CRP conjugate is diluted in buffer containing protein and salt stabilizers and 0.1% $NaN_3$ as preservative, to give a net intensity reading of 3000 at gain of 20 on the TDx Analyzer.

Antiserum: Dilutions of raw CRP antiserum is diluted at from 1:10 to 1:100. 25 ul of each dilution is added to a cuvette and allowed to incubate with 25 ul of tracer reagent in 2 ml final volume of 0.1 M Phosphate buffer, pH 7.5, 0.01% Bovine-gamma ethylene glyco-Globulin (BGG), 0.1% $NaN_3$ and 2% (by Volume). The antiserum and tracer react for 3.4 minutes at 35° C. in the above buffered conditions. A dilution factor is determined for the antiserum which is based on the fluorescence polarization measured. The antiserum reagent is then prepared in the above phosphate buffer by diluting the raw antiserum according to the determined dilution factor.

Pretreatment:

Pretreatment ("popper") reagent consists of a solution of an anionic surfactant in 0.05 Molar Tris, pH 8.0, 0.1% $NaN_3$ as preservative and other organic stabilizing solvents.

Buffer:

TDx assay buffer consists of 0.1 Molar Phosphate, pH 7.5, 0.01% Bovine-gamms-Globulin (BGG) and 0.1% $NaN_3$ as a preservative.

Calibrators:

C-Reactive protein is placed in buffered synthetic serum matrix containing protein and salt stabilizers and 0.1% $NaN_3$ as a preservative.

Controls:

(Contained in the same matrix as calibrators)

| Stabilizing Media Reagent Composition For DTAF/CRP Tracer | | |
|---|---|---|
| Constituent | Concentration grams/liter | Other |
| Trigmo Base (Tris) | 12.11 | (0.1 Molar) |
| $Na_2SO_4$ (Anhydrous) | 20.0 | (2%) |
| Oval bumin Hydrolysate | 5.0 | (0.5%) |
| Propylene Glycol | 20.0 ml | (2% by volume) |
| $CaCl_2\ 2H_2O$ | 0.294 | (0.002 Molar) |
| $NaN_3$ | 1.0 | (0.1%) |
| Adjust pH with: 6 N HCl to 7.0 | | |
| Acceptable variations of the above formula: pH range 6-8 | | |
| $Na_2SO_4$ concentration at 4% and 0.2% Oval bumin at pH 7.0 | | |
| Substitute 2% E hylene glycol for 2% Propylene glycol | | |
| Substitute $Na_2SO_4$ with $(NH_4)_2SO_4$, Oval bumin Hydrolysate with oval bumin. | | |

The above formulation has been found to sterilize the CRP-DTAF conjugate for 10 days at 45° C. stabilizing medice reagent composition for calibrators/controls.

| Constituent | Concentration grams/liter | Other |
|---|---|---|
| Trigmo Base (Tris) | 12.11 | (0.1 Molar) |
| Na$_2$SO$_4$ | 8.0 | (8.0%) |
| Oval bumin Hydrolysate | 10.0 | (1.0%) |
| CaCl$_2$ 2H$_2$O | 0.294 | (0.002 Molar) |
| NaN$_3$ | 1.0 | (0.1%) |

The pH is adjacent with 6 N HCl to pH 8.0.

The above formulation has been found to stabilize C-Revitive protein for 30 days at 45° C.

Pretreatment Reagent Composition

| Constituent | Concentration | grams or milliliter/ liter |
|---|---|---|
| Tris | 0.05 Molar | 6.06 g |
| NaN$_3$ | 0.1% | 1.00 g |
| 2-Propanol | 10% by Volume | 100.0 ml |
| DMSO | 20% by Volume | 200.0 ml |
| Propylene Glycol | 5% by Volume | 20.0 ml |
| Dioctyl Sodium Sulfosuccinate at 60% Stock Concentration | 4% | 66.67 ml |

The pH is adjusted to 8.0 with 6 N HCl. This pretreatment composition has been found to be effective in eliminating Bilirubin interference at Bilirubin concentrations of 20 mg/d/ while using a CRP assay sample volume of 8.0 microliters.

Assay Procedure

A fluorescence polarization immunoassay (FPIA) for CRP is carried out on the TDx Fluorescense Polarization Analyzer as follows. The reaction sequence, incubation, timing, regent volumes and sample volumes are microprocessor controlled according to programmed assay parameters. To perform the CRP assay, specimens and reagents are loaded on the TDx Analyzer, in their respective receptacles. Specimen, antiserum, popper and buffer are dispensed into the reaction well. One-half of the final volume of the diluted specimen is dispensed into the cuvette along with sufficient buffer to give one-half the final reaction volume. A background intensity reading is taken on the mixture of specimen, antiserum and popper. The second half of the diluted speciment is dispensed into the cuvette with tracer and buffer to provide the final reaction volume of 2 ml. The final intensity measurement is then made. The specific assay sequence for performing the TDx/CRP procedure comprises the following steps:

1. 8.6 microliter of specimen are dispensed into the reaction well, and 25 microliters of buffer are added.

2. 10 microliters of popper reagent and 25 microliters of antiserum reagent are added to the specimen in the reaction well and 431.4 microliters of buffer are added to bring the final reaction well volume to 500 microliters.

3. An additional 25 microliters of popper reagent are dispensed to the cuvette.

4. 174 microliters of the specimen, antiserum and popper mixture contained in the reaction well is transferred to the cuvette, and diluted with 776 microliters of buffer, to obtain an intermediate cuvette colume of 1000 microliters.

Note: Steps 1-4 are repeated for each sample and are accomplished in 18.4 seconds per sample.

5. The cuvette contents are incubated for 6.4 minutes at 34° C. while a background reading is taken at 3.4 minutes and stored for each speciment.

6. Following the background recording, an additional 174 microliters of specimen, antiserum and popper mixture is transferred from the reaction well to the cuvette and 20 microliters of buffer are added.

7. 25 microliters of tracer reagent are added to the cuvette and sufficient buffer added (601 microliters) to give a final cuvette colume of 2 ml.

8. The final cuvette reaction mixture is incubated for 3.4 minutes and a final reading taken for each specimen.

9. The blank reading is subtracted from the final reading and net polarization reading is reported for each specimen.

10. The net polarization reading is converted to a CRP concentration by utilizing four stored mathematical constants derived from a calibration curve, previously generated with calibratores of known CRP concentration. The four constants are determined by a least-square curve-fit four parameter program which is part of the data-handling system associated with the TDx Analyzer.

Utilizing the assay performed according to the invention, as previously described, recovery of CRP added to a specimen containing normal levels of CRP to give approximate concentrations of 2, 10 and 20 mg/d/CRP was 100%, 100% and 99.6%, respectively. To two other samples containing slightly elevated levels of CRP, and approximate concentration of 10 mg/d/ was added. The recovery from these samples was 98.9% and 97.4%. Results are summarized below.

| Initial Sample CRP Conc. mg/d/ | Concentrated CRP Added mg/d/ | Measured CRP Conc. mg/d/ | % Recovery |
|---|---|---|---|
| .15 | 2.19 | 2.34 | 100 |
| .15 | 10.96 | 11.11 | 100 |
| .15 | 21.92 | 21.99 | 99.6 |
| 1.73 | 9.55 | 11.17 | 98.9 |
| 1.68 | 9.55 | 10.98 | 97.4 |

Correlation with Other Methods:

Human Serum specimens were obtained for a period of one and one-half months from a patient population requested for CRP testing. A CRP value for each specimen was generated at the hospital utilizing a commercial nephelometric method. Samples were transported frozen, then tested by the CRP assay of the invention as aforedescribed. Patient results from both methods were compared by linear regression analysis. The following results are indicated for the 345 specimens tested:

| Correlation Coefficient | = | 0.992 |
|---|---|---|
| Slope | = | .976 |
| y-intercept | = | 3.0 micrograms/ml |

A field study was conducted at a local hospital for approximately two weeks. During this period seventy climiol specimens were tested, using three methods: Nephelomethyl (NPM), radialimmunodiffusion (RID) and the assay according to the invention as previously described (TDx CRP). Correlation data from the three methods as summarized below.

| Method Compared | Slope | Intercept | r |
| --- | --- | --- | --- |
| TDx CRP vs. NPM CRP | 1.06 | −0.17 | 0.99 |
| TDx CRP vs. RID CRP | 0.97 | 0.40 | 0.99 |
| NPM CRP vs. RID CRP | 0.91 | 0.50 | 0.98 |

Assay Sensitivity

A detection limit of 0.3 mg/d/ was based on two standard derivatives taken away from the millipolarization (mP) means of twenty "zero" calibrator replicates. The resulting mP was then read of the calibration curve found to correspond to a CRP concentration of 0.3 mg/d/.

$X_{20} = 270.55$ mP

Std. Dev. $= 0.529$ mP

Std. Dev's. $= 1.06$ mP $= 0.3$ mg/d/

It is apparent that various modifications and variations that can be made by one skilled in the art from the specific disclosure of the invention herein contained, without departing from the spirit and scope of the invention, as defined solely in the following claims.

What is claimed is:

1. A method for determining the presence of concentration of C-reactive protein in a liquid sample of biological fluid, comprising intermixing with a sample of said biological fluid a fluorescent tracer comprising a conjugate of C-reactive protein and a fluorescent moiety, so as to be specifically recognizable by a common antibody or receptor binding site with a solution of an antibody capable of specifically recognizing the C-reactive protein in the sample and the tracer; and determining the amount of the tracer which becomes bound to the antibody by fluorescence polarization as a measure of the amount of C-reactive protein in the sample.

2. The method of claim 1 where said step (a) is conducted at a pH sufficient to maintain said fluorescent tracer in an ionized state.

3. The method of claim 1 where said fluorescent moiety is 5(4,6-dichlorotriazin-2-yl)-amino fluorescein.

4. A compound useful in a fluorescence polarization assay for determining the presence or amount of a C-reactive protein in a liquid sample of a biological fluid, which compound consisting of C-reactive protein conjugated to 5(4,6-dichlorotriazin-2-yl)amino fluorescein.

* * * * *